(12) United States Patent
Justis et al.

(10) Patent No.: US 9,066,758 B2
(45) Date of Patent: Jun. 30, 2015

(54) SPINAL IMPLANT SYSTEM AND METHOD

(75) Inventors: Jeff R. Justis, Germantown, TN (US);
Larry T. McBride, Memphis, TN (US);
John Stewart Young, Olive Branch, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 309 days.

(21) Appl. No.: 13/588,686

(22) Filed: Aug. 17, 2012

(65) Prior Publication Data

US 2014/0052180 A1    Feb. 20, 2014

(51) Int. Cl.
*A61B 17/70* (2006.01)

(52) U.S. Cl.
CPC ......... *A61B 17/7032* (2013.01); *A61B 17/7082* (2013.01)

(58) Field of Classification Search
CPC ........... A61B 17/7074; A61B 17/7076; A61B 17/7077; A61B 17/7079; A61B 17/708; A61B 17/7083; A61B 17/7085; A61B 17/7086; A61B 17/7088; A61B 17/7089; A61B 17/7091; A61B 17/7082
USPC ......... 606/246–279, 104, 86 A, 86 B, 99, 305
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno et al. | |
| 5,891,145 A | 4/1999 | Morrison et al. | |
| 7,226,413 B2 | 6/2007 | McKinley | |
| 7,462,182 B2 * | 12/2008 | Lim | 606/99 |
| 7,476,240 B2 | 1/2009 | Raymond et al. | |
| 7,491,218 B2 | 2/2009 | Landry et al. | |
| 7,563,264 B2 | 7/2009 | Landry et al. | |
| 7,575,581 B2 * | 8/2009 | Lovell | 606/104 |
| 7,597,694 B2 * | 10/2009 | Lim et al. | 606/86 A |
| 7,666,189 B2 | 2/2010 | Gerber et al. | |
| 7,758,584 B2 * | 7/2010 | Bankoski et al. | 606/104 |
| 7,794,464 B2 | 9/2010 | Bridwell et al. | |
| 7,802,547 B2 | 9/2010 | Inomoto et al. | |
| 7,842,044 B2 | 11/2010 | Runco et al. | |
| 7,846,093 B2 | 12/2010 | Gorek et al. | |
| 7,854,751 B2 | 12/2010 | Sicvol et al. | |
| 7,887,541 B2 | 2/2011 | Runco et al. | |
| 7,914,558 B2 | 3/2011 | Landry et al. | |
| 7,918,857 B2 | 4/2011 | Dziedzic et al. | |
| 7,918,858 B2 | 4/2011 | Stad et al. | |
| 7,922,746 B2 | 4/2011 | Miller | |
| 7,927,334 B2 | 4/2011 | Miller et al. | |
| 7,931,673 B2 * | 4/2011 | Hestad et al. | 606/246 |
| 7,947,046 B2 * | 5/2011 | Justis et al. | 606/86 A |
| 7,951,175 B2 * | 5/2011 | Chao et al. | 606/279 |

(Continued)

*Primary Examiner* — Eduardo C Robert
*Assistant Examiner* — Lynnsy Summitt
(74) *Attorney, Agent, or Firm* — Sorell Lenna & Schmidt LLP

(57) ABSTRACT

An extender comprises an outer member including a lateral opening, first and second extensions defining first and second axial cavities, the axial cavities including a first portion, a second portion and a third portion. An inner member includes a body defining a tab, first and second arms having first and second projections. The inner member is configured for axial translation relative to the outer member between a first position, a second position and a third position. The tab is movable into at least one locking cavity of the lateral opening to fix the inner member relative to the outer member. Methods of use are disclosed.

20 Claims, 14 Drawing Sheets

(56) References Cited

U.S. PATENT DOCUMENTS

| | | |
|---|---|---|
| 7,985,242 B2 | 7/2011 | Forton et al. |
| 8,012,141 B2 | 9/2011 | Wright et al. |
| 8,096,996 B2 | 1/2012 | Gutierrez et al. |
| 8,235,997 B2 * | 8/2012 | Hoffman et al. ............ 606/86 A |
| 8,323,286 B2 * | 12/2012 | Justis ......................... 606/86 A |
| 8,439,922 B1 * | 5/2013 | Arnold et al. ............... 606/86 A |
| 8,439,924 B1 * | 5/2013 | Mcbride et al. ............ 606/86 A |
| 8,460,300 B2 * | 6/2013 | Hestad et al. .............. 606/86 A |
| 8,545,505 B2 * | 10/2013 | Sandstrom et al. ......... 606/86 A |
| 8,617,218 B2 * | 12/2013 | Justis et al. ................... 606/278 |
| 8,709,044 B2 * | 4/2014 | Chao et al. .................... 606/246 |
| 2006/0074418 A1 | 4/2006 | Jackson |
| 2006/0079903 A1 | 4/2006 | Wong |
| 2006/0111712 A1 | 5/2006 | Jackson |
| 2006/0111715 A1 | 5/2006 | Jackson |
| 2006/0111730 A1 | 5/2006 | Hay |
| 2006/0122597 A1 | 6/2006 | Jones et al. |
| 2006/0264962 A1 | 11/2006 | Chin et al. |
| 2006/0293680 A1 | 12/2006 | Jackson |
| 2007/0213714 A1 | 9/2007 | Justis |
| 2007/0244493 A1 | 10/2007 | Bjerken |
| 2007/0270867 A1 | 11/2007 | Miller et al. |
| 2008/0015601 A1 * | 1/2008 | Castro et al. ................... 606/86 |
| 2008/0172062 A1 | 7/2008 | Donahue et al. |
| 2008/0228233 A1 * | 9/2008 | Hoffman et al. ............ 606/86 A |
| 2008/0234678 A1 | 9/2008 | Gutierrez et al. |
| 2008/0243190 A1 | 10/2008 | Dziedzic et al. |
| 2009/0105771 A1 | 4/2009 | Lei et al. |
| 2009/0143828 A1 | 6/2009 | Stad et al. |
| 2009/0157125 A1 * | 6/2009 | Hoffman et al. ............ 606/86 A |
| 2009/0171391 A1 | 7/2009 | Hutton et al. |
| 2009/0222046 A1 | 9/2009 | Gorek |
| 2009/0228054 A1 * | 9/2009 | Hoffman et al. ............ 606/86 A |
| 2009/0228055 A1 * | 9/2009 | Jackson ....................... 606/86 A |
| 2009/0228056 A1 | 9/2009 | Jackson |
| 2009/0234395 A1 | 9/2009 | Hoffman et al. |
| 2009/0264895 A1 | 10/2009 | Gasperut et al. |
| 2009/0318972 A1 | 12/2009 | Jackson |
| 2010/0030283 A1 | 2/2010 | King et al. |
| 2010/0036443 A1 | 2/2010 | Hutton et al. |
| 2010/0063552 A1 | 3/2010 | Chin et al. |
| 2010/0069972 A1 | 3/2010 | Jones et al. |
| 2010/0198268 A1 | 8/2010 | Zhang et al. |
| 2010/0198271 A1 | 8/2010 | Leone |
| 2010/0312279 A1 | 12/2010 | Gephart et al. |
| 2011/0015678 A1 | 1/2011 | Jackson |
| 2011/0022088 A1 | 1/2011 | Forton et al. |
| 2011/0022093 A1 * | 1/2011 | Sherman et al. ............. 606/254 |
| 2011/0040335 A1 * | 2/2011 | Stihl et al. ..................... 606/302 |
| 2011/0087298 A1 * | 4/2011 | Jones .......................... 606/86 A |
| 2011/0106178 A1 | 5/2011 | Schwab |
| 2011/0202096 A1 | 8/2011 | White et al. |
| 2011/0218581 A1 * | 9/2011 | Justis .......................... 606/86 A |
| 2011/0264098 A1 | 10/2011 | Cobbs |
| 2013/0018419 A1 * | 1/2013 | Rezach et al. ................ 606/264 |
| 2013/0041415 A1 * | 2/2013 | Justis .......................... 606/86 A |
| 2013/0261679 A1 * | 10/2013 | McBride et al. ............ 606/86 A |
| 2014/0148865 A1 * | 5/2014 | Hennard et al. ............. 606/86 A |

* cited by examiner

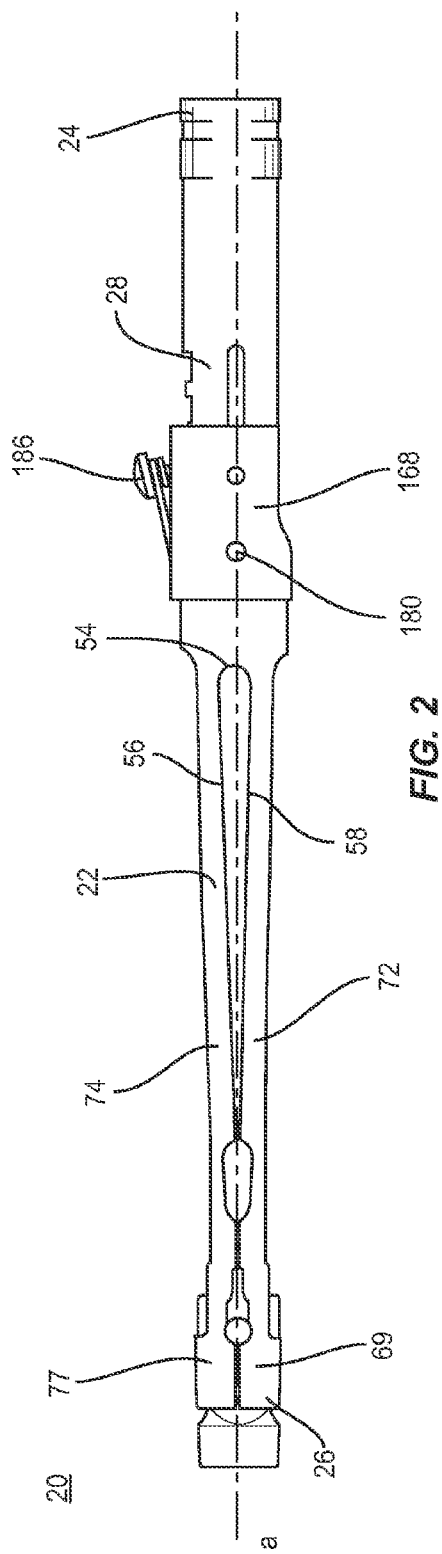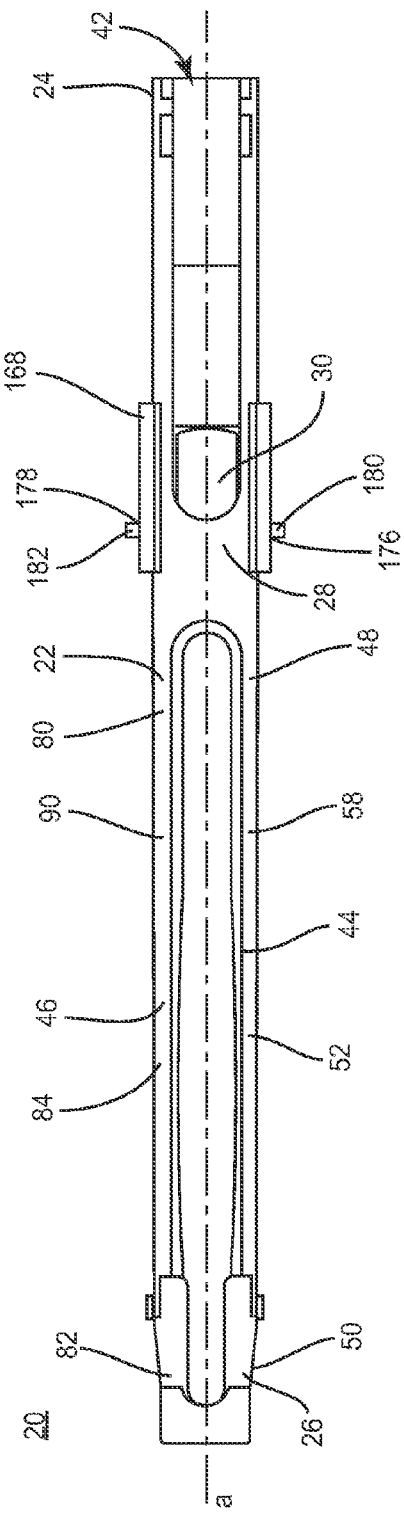

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, an extender is provided. The extender comprises an outer member defining a longitudinal axis and including a body defining a lateral opening. The outer member includes a first extension defining a first axial cavity and a second extension defining a second axial cavity. Each of the axial cavities including a first portion, a second portion and a third portion. An inner member includes a body defining a tab configured for disposal in the lateral opening. The inner member includes a first arm having a first projection disposed for movement within the first axial cavity and a second arm having a second projection disposed for movement within the second axial cavity. The inner member is configured for axial translation relative to the outer member such that the projections are disposable between a first position such that the projections are disposed with the first portions of the respective axial cavity and the outer member is disposed in a non-expanded orientation, a second position such that projections are disposed with the second portions of the respective axial cavity and the outer member is disposed in an expanded orientation, and a third position such that the projections are disposed with the third portions of the respective axial cavity and the outer member is disposed in an expanded orientation. The lateral opening includes at least one locking cavity such that the tab is movable into the at least one locking cavity to fix the inner member relative to the outer member in at least one of the positions.

In one embodiment, the extender comprises an outer member defining a longitudinal axis and including a first extension defining a first axial cavity and a second extension defining a second axial cavity. Each of the axial cavities including a first portion having a first dimension, a second portion having a second dimension and a third portion having a third dimension. The first dimension is greater than the second dimension and the second dimension is greater than the third dimension. An inner member includes a first arm having a first outward projection disposed for movement within the first axial cavity and a second arm having a second outward projection disposed for movement within the second axial cavity. The inner member is configured for axial translation relative to the outer member such that the projections are disposable between a first position such that the projections are disposed with the first portions of the respective axial cavity and the outer member is disposed in a non-expanded orientation, a second position such that the projections are disposed with the second portions of the respective axial cavity and the outer member is disposed is disposed in a first expanded orientation, and a third position such that the projections are disposed with the third portions of the respective axial cavity and the outer member is disposed in a second expanded orientation.

In one embodiment, a spinal implant system is provided comprising an extender comprising an outer sleeve extending between a proximal end and a distal end and defining a longitudinal axis and inner sleeve extending between a proximal end and a distal end. The outer sleeve including a body defining a lateral opening. The lateral opening including a proximal lock slot, an intermediate lock slot and a distal lock slot disposed in series along the longitudinal axis. The outer sleeve including a first wall extending from the body and having a first extension including a first cantilever and a second cantilever defining a first axial cavity therebetween. A second extension includes a first cantilever and a second cantilever defining a second axial cavity therebetween. Each of the axial cavities including a distal portion having a first dimension, an intermediate portion having a second dimension and a proximal portion having a third dimension. The first dimension is greater than the second dimension and the second dimension is greater than the third dimension. Each of the cantilevers including a capture surface. The inner sleeve including a body defining a resilient tab such that the tab is rotatable relative to the inner member body. The inner sleeve includes a first arm having a first outward projection disposed for movement within the first axial cavity and a second arm having a second outward projection disposed for movement within the second axial cavity. The first arm includes a first flange that defines a first flange cavity configured for disposal of the first extension such that the first flange slidably engages the first extension during axial translation. The second arm includes a second flange that defines a second flange cavity configured for disposal of the second extension such that the second flange slidably engages the second extension during axial translation. A tubular actuator is disposed about the outer sleeve and connected with the inner sleeve. The actuator defines a resilient button rotatable relative to the actuator. A bone fastener includes a proximal portion that defines an implant cavity and a distal portion configured to penetrate tissue. The inner sleeve is configured for axial translation relative to the outer sleeve such that the outward projections are disposable between a first position such that the outward projections are disposed with the distal portions of the respective axial cavity and the outer sleeve is disposed in a locking orientation, a second position such that the outward projections are disposed with the intermediate portions of the respective axial cavity and the outer sleeve is disposed in a capture orientation, and a third position such that the outward projections are is disposed with the second portions of the respective axial cavity and the outer sleeve is disposed in an eject orientation. The button engages the tab to rotate the tab relative to the inner sleeve body into the distal lock slot to fix the inner member relative to the outer member in the first position, the intermediate lock slot to fix the inner member relative to the outer member in the second position and the proximal lock slot to fix the inner member relative to the outer member in the third position.

BRIEF DESCRIPTION OF THE DRAWINGS

The present disclosure will become more readily apparent from the specific description accompanied by the following drawings, in which:

FIG. 2 is a side view of the system shown in FIG. 1;

FIG. 3 is a side view of the system shown in FIG. 1;

Like reference numerals indicate similar parts throughout the figures.

DETAILED DESCRIPTION

Figure 1:
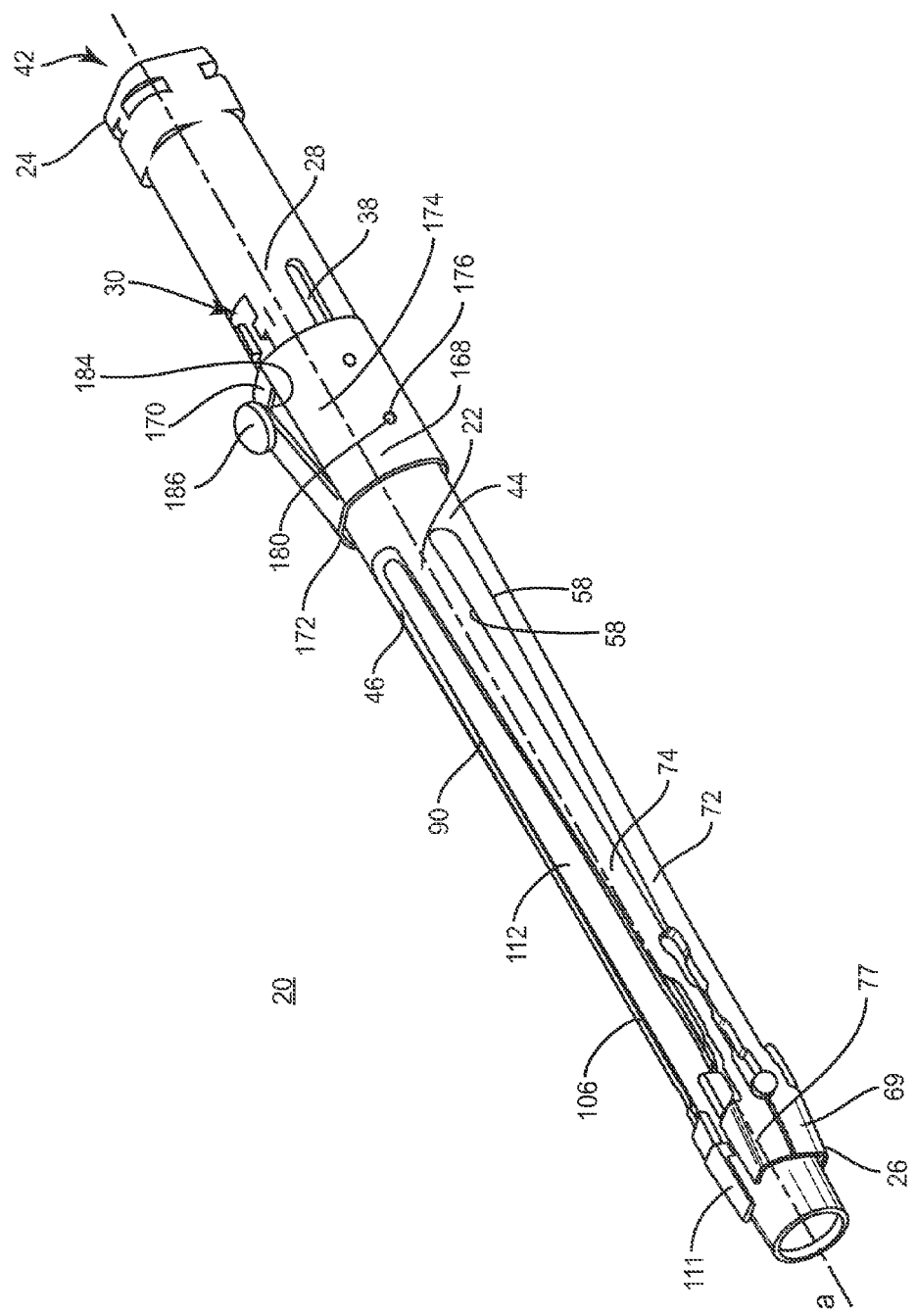
FIG. 1 is a perspective view of one particular embodiment of a system in accordance with the principles of the present disclosure.
Figure 4:
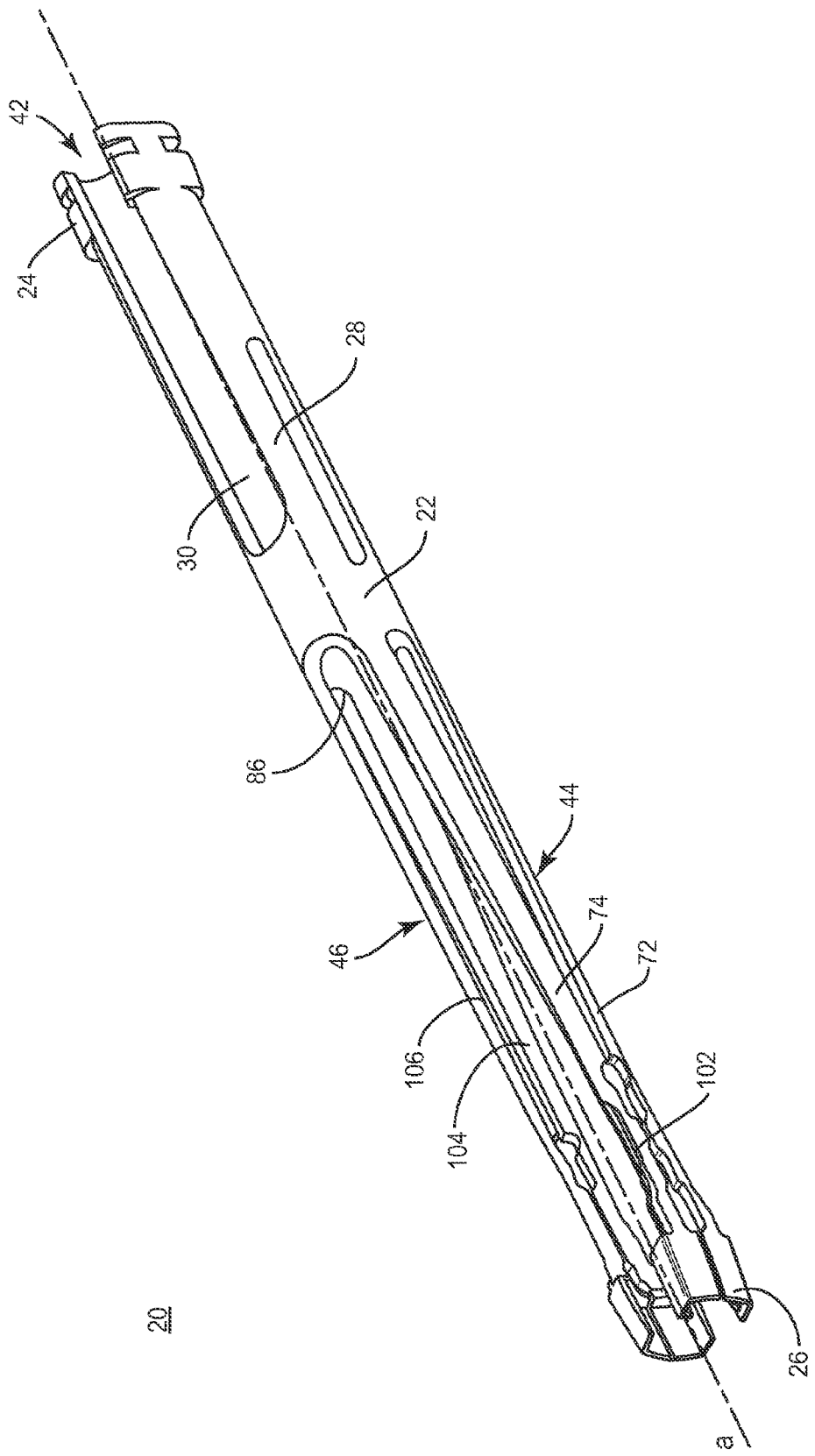
FIG. 4 is a perspective view of a component of the system shown in FIG. 1.
Figure 5:
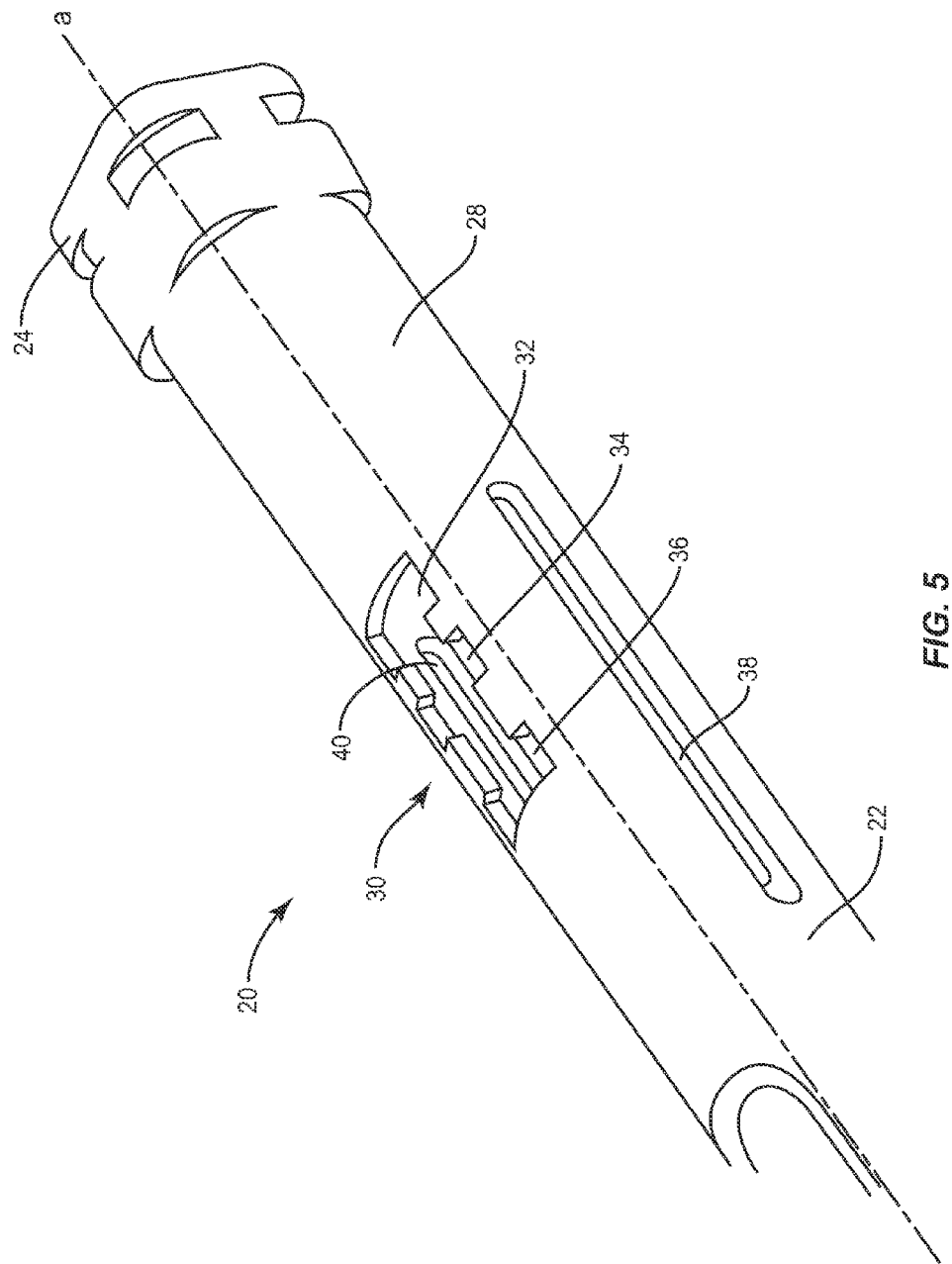
FIG. 5 is a break away perspective view of the component shown in FIG. 4.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical implant system can include a bone fastener having a head with a configuration that allows the head to be captured and retained under tension and lateral compression. It is further envisioned that the tension may be applied through a member, such as, for example, an extender and that compression may be applied through another member, such as, for example, a sleeve.

In one embodiment, the surgical implant system provides an implant loading configuration including a locking orientation, a capture orientation and/or an eject orientation. In one embodiment, the surgical implant system includes an outer sleeve. The outer sleeve may include a square connection geometry for use with a bar inserter and/or sequential reduction sleeve. The outer sleeve may include arms that open and close to hold an implant such as a screw. The outer sleeve may include openings such as cuts to provide stops for an implant loading configuration. In one embodiment, the surgical implant system includes an inner sleeve. The inner sleeve may include a tab configured to engage the outer sleeve in various positions. The inner sleeve may include a post that engages the outer sleeve to open and close arms of the outer sleeve. The inner sleeve may include rails to secure the inner sleeve with arms of the outer sleeve. The inner sleeve may define a cavity configured to facilitate set screw insertion and tool passage.

It is envisioned that the system may include instruments that are connected or attached to an extender(s) such as, for example, a lateral translation handle or derotaton instruments. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower"

are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-14, there is illustrated components of a surgical system, such as, for example, a spinal implant system 20 in accordance with the principles of the present disclosure.

The components of spinal implant system 20 can be fabricated from biologically acceptable materials suitable for medical applications, including metals, synthetic polymers, ceramics and bone material and/or their composites, depending on the particular application and/or preference of a medical practitioner. For example, the components of spinal implant system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that spinal implant system 20 and the methods disclosed may be employed with treatments using minimally invasive and percutaneous techniques.

Spinal implant system 20 includes an outer member, such as, for example, an outer sleeve 22. Outer sleeve 22 has a cylindrical cross-section configuration. It is contemplated that the cross-section of outer sleeve 22 may have various configurations, for example, round, oval, rectangular, polygonal, irregular, tapered, offset, staggered, uniform and non-uniform. It is further envisioned that one or all of the surfaces of outer sleeve 22 may have alternate surface configurations, such as, for example, rough, threaded for connection with surgical instruments, arcuate, undulating, porous, semi-porous, dimpled, polished and/or textured according to the requirements of a particular application.

Outer sleeve 22 extends between a proximal end 24 and a distal end 26. Outer sleeve 22 defines a longitudinal axis a. Proximal end 24 includes body 28. Body 28 defines a lateral opening 30. Opening 30 defines a first lock slot, such as, for example, a proximal lock slot 32, a second lock slot, such as, for example, an intermediate lock slot 34 and a third lock slot, such as, for example, a distal lock slot 36. Opening 30 is configured for engagement with an actuator, as described herein. Body 28 defines passages 38 and 40. Passages 38, 40 are disposed on parallel sides of body 28. Passages 38, 40 are configured for slidable engagement with an actuator, as described herein.

Outer sleeve 22 includes a cavity, such as, for example, channel 42 that extends through outer sleeve 22. Channel 42 has a circular cross-section configuration. It is contemplated that the cross-section of channel 42 may have various configurations, for example, round, oval, rectangular, polygonal, irregular, tapered, offset, staggered, uniform and non-uniform. Channel 42 is configured for disposal of implants, such as spinal rods and screws and/or instruments, such as drivers and reduction devices. In one embodiment, channel 42 is configured for disposal and movable passage therethrough of instruments, such as, for example, torque devices, screw drivers, extenders, inserters, reducers, rod delivery adaptors, bone fasteners and/or vertebral constructs, which may be alternately sized and dimensioned.

Outer sleeve 22 includes two spaced apart extensions comprising a first extension 44 and a second extension 46. Extension 44 extends between a proximal end 48 and a distal end 50. An intermediate portion 52 is disposed between ends 48, 50. Extension 44 includes a wall 54. It is envisioned that wall 54 may have uniformly increasing or decreasing taper, arcuate, staggered and/or offset portions. Wall 54 includes a first cantilever 72 and a second cantilever 74 extending from proximal end 48. Cantilevers 72, 74 are resiliently biased inwardly towards each other and/or in a convergent configuration to a non-expanded orientation of outer sleeve 22.

Figure 12:
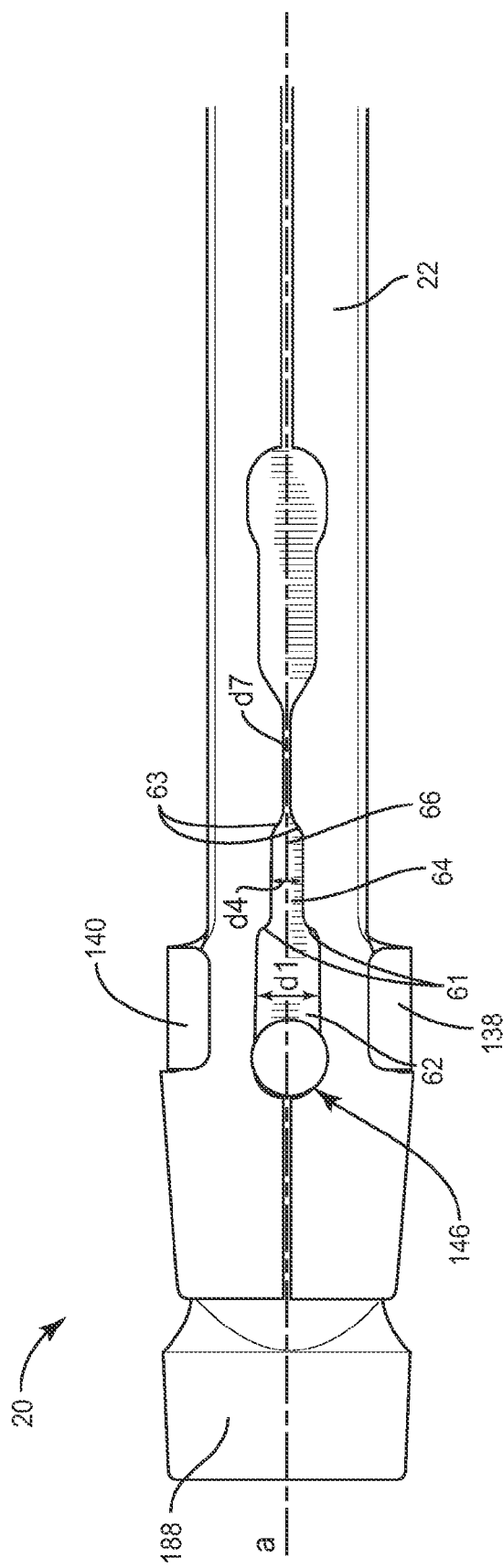
FIG. 12 is an enlarged break away view of the system shown in FIG. 1.

Wall 54 includes a first surface 56 and a second surface 58. Surfaces 56, 58 are spaced apart to define an axial cavity 60 that is disposed adjacent distal end 50. Axial cavity 60 includes a first portion, such as, for example, a distal portion 62, a second portion, such as, for example, an intermediate portion 64 and a third portion, such as, for example, a proximal portion 66, as shown in FIG. 12. Axial cavity 60 is configured for slidable disposal of a pin and an inner sleeve, as described herein.

Figure 13:
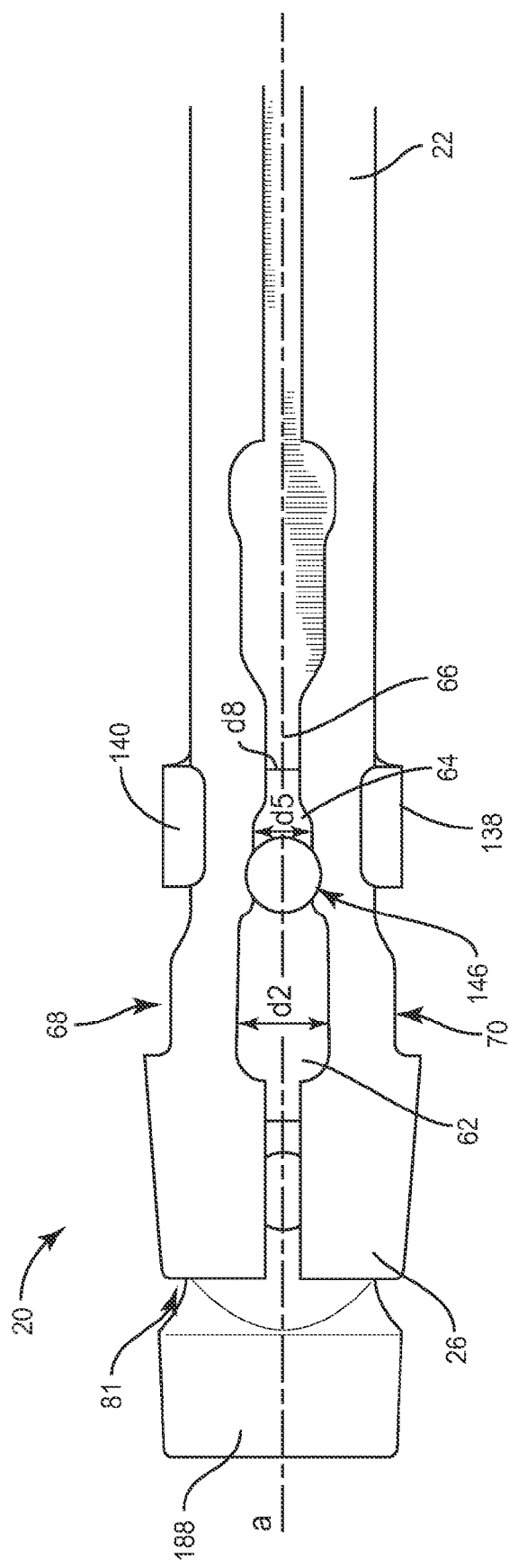
FIG. 13 is an enlarged break away view of the system shown in FIG. 1.
Figure 14:
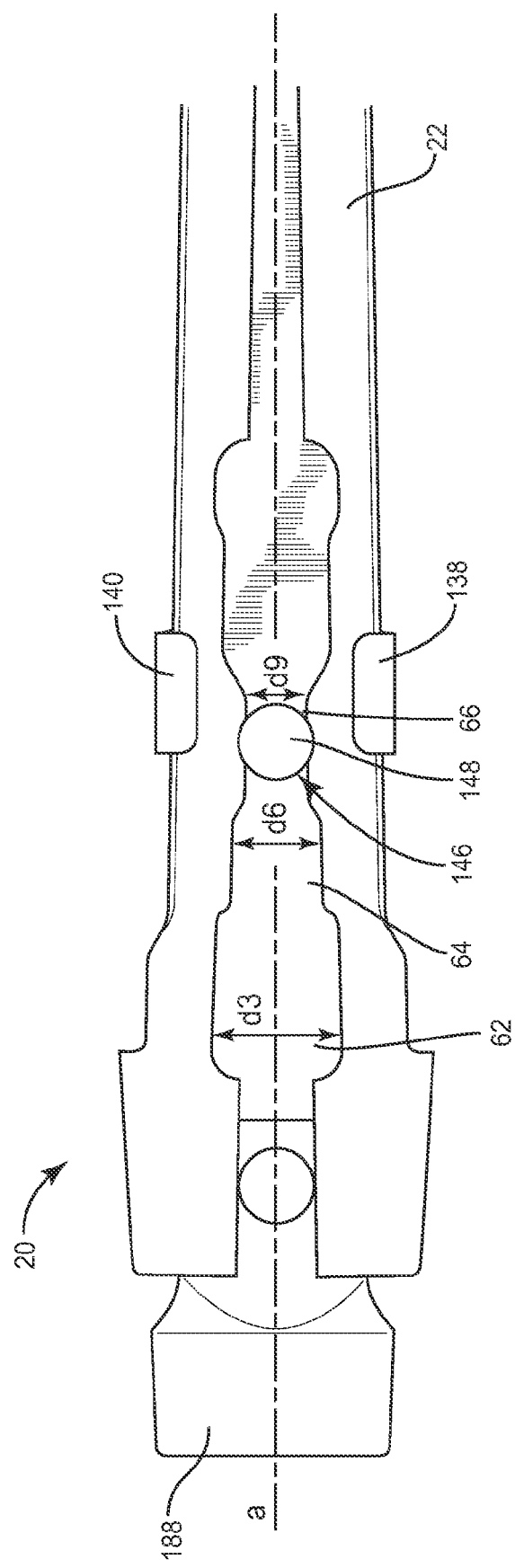
FIG. 14 is an enlarged break away view of the system shown in FIG. 1.

Surfaces 56, 58 are spaced apart a distance d1 adjacent distal portion 62 in a non-expanded orientation of outer sleeve 22. Outer sleeve 22 is expandable to a first expanded orientation, as shown in FIG. 13, such that surfaces 56, 58 are spaced apart a distance d2 adjacent distal portion 62. Outer sleeve 22 is expandable to a second expanded orientation, as shown in FIG. 14, such that surfaces 56, 58 are spaced apart a distance d3 adjacent distal portion 62. As such, axial cavity 60 can be expanded and contracted adjacent distal portion 62 within a range of expansion between distance d1, distance d2 and distance d3. Distance d3 has a dimension greater than distance d2 and distance d2 has a dimension greater than distance d1.

Ramps 61 are disposed between distal portion 62 and intermediate portion 64. Ramps 61 extend between a proximal end and a distal end, which define an inclination for engagement with the inner sleeve that facilitates expansion of outer sleeve 22 between the non-expanded orientation, the first expanded orientation and the second expanded orientation.

Surfaces 56, 58 are spaced apart a distance d4 adjacent intermediate portion 64 in the non-expanded orientation of outer sleeve 22, as shown in FIG. 12. Outer sleeve 22 is expandable to the first expanded orientation, as shown in FIG. 13, such that surfaces 56, 58 are spaced apart a distance d5 adjacent intermediate portion 64. Outer sleeve 22 is expandable to the second expanded orientation, as shown in FIG. 14, such that surfaces 56, 58 are spaced apart a distance d6 adjacent intermediate portion 64. As such, axial cavity 60 can be expanded and contracted adjacent intermediate portion 64 within a range of expansion between distance d4, distance d5 and distance d6. Distance d6 has a dimension greater than distance d5 and distance d5 has a dimension greater than distance d4.

Ramps 63 are disposed between intermediate portion 64 and proximal portion 66. Ramps 63 extend between a proximal end and a distal end, which define an inclination for engagement with the inner sleeve that facilitates expansion of outer sleeve 22 between the non-expanded orientation, the first expanded orientation and the second expanded orientation.

Surfaces 56, 58 are spaced apart a distance d7 adjacent proximal portion 66 in the non-expanded orientation of outer sleeve 22, as shown in FIG. 12. Outer sleeve 22 is expandable to the first expanded orientation, as shown in FIG. 13, such that surfaces 56, 58 are spaced apart a distance d8 adjacent proximal portion 66. Outer sleeve 22 is expandable to the second expanded orientation, as shown in FIG. 14, such that surfaces 56, 58 are spaced apart a distance d9 adjacent proximal portion 66. As such, axial cavity 60 can be expanded and contracted adjacent proximal portion 66 within a range of expansion between distance d7, distance d8 and distance d9. Distance d9 has a dimension greater than distance d8 and distance d8 has a dimension greater than distance d7.

In one embodiment, d1 is greater than d4 and d4 is greater than d7. In one embodiment, d2 is greater than d5 and d5 is greater than d8. In one embodiment, d3 is greater than d6 and d6 is greater than d9.

Figure 6:
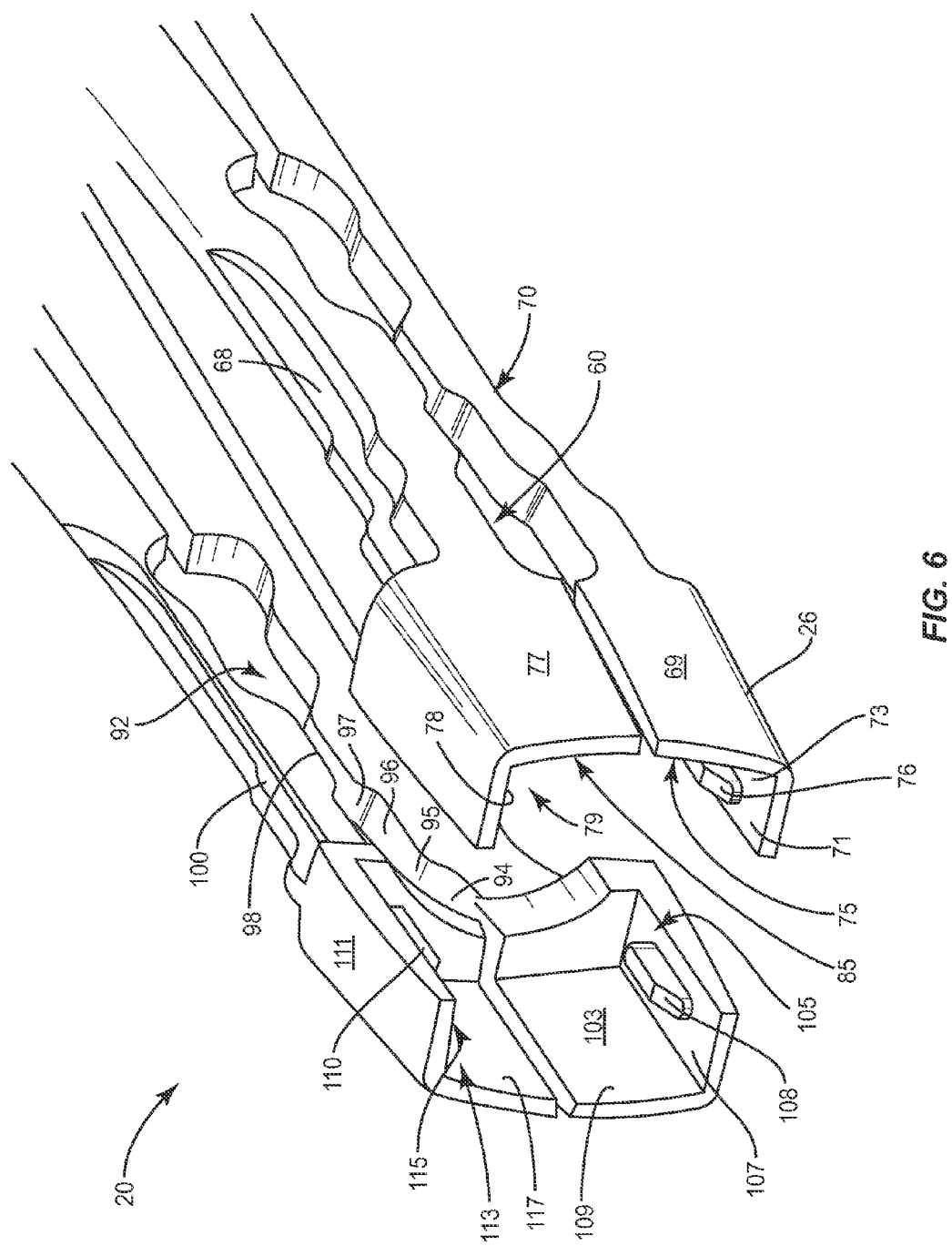
FIG. 6 is a break away perspective view of the component shown in FIG. 4.
Figure 7:
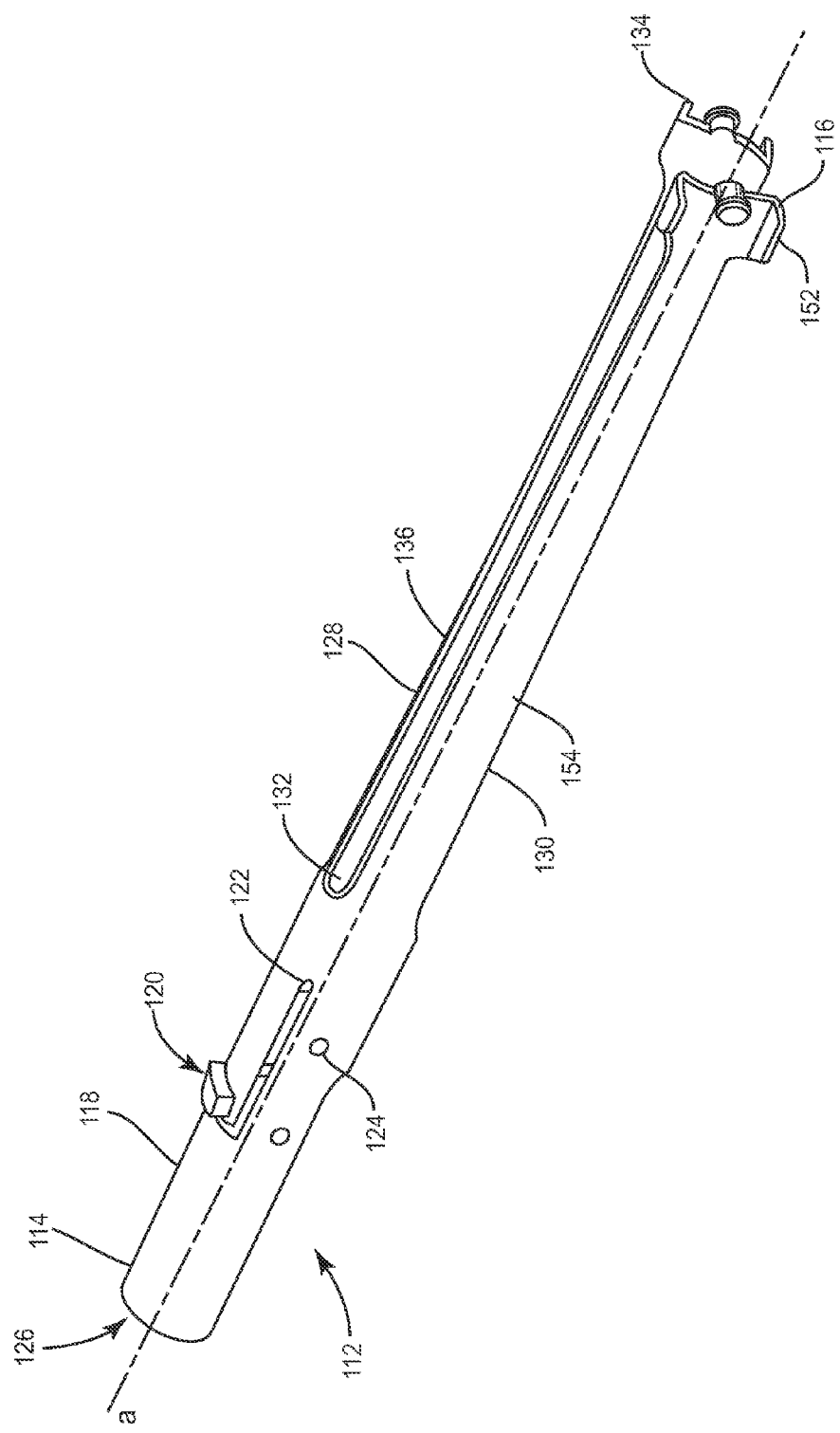
FIG. 7 is a perspective view of a component of the system shown in FIG. 1.
Figure 8:
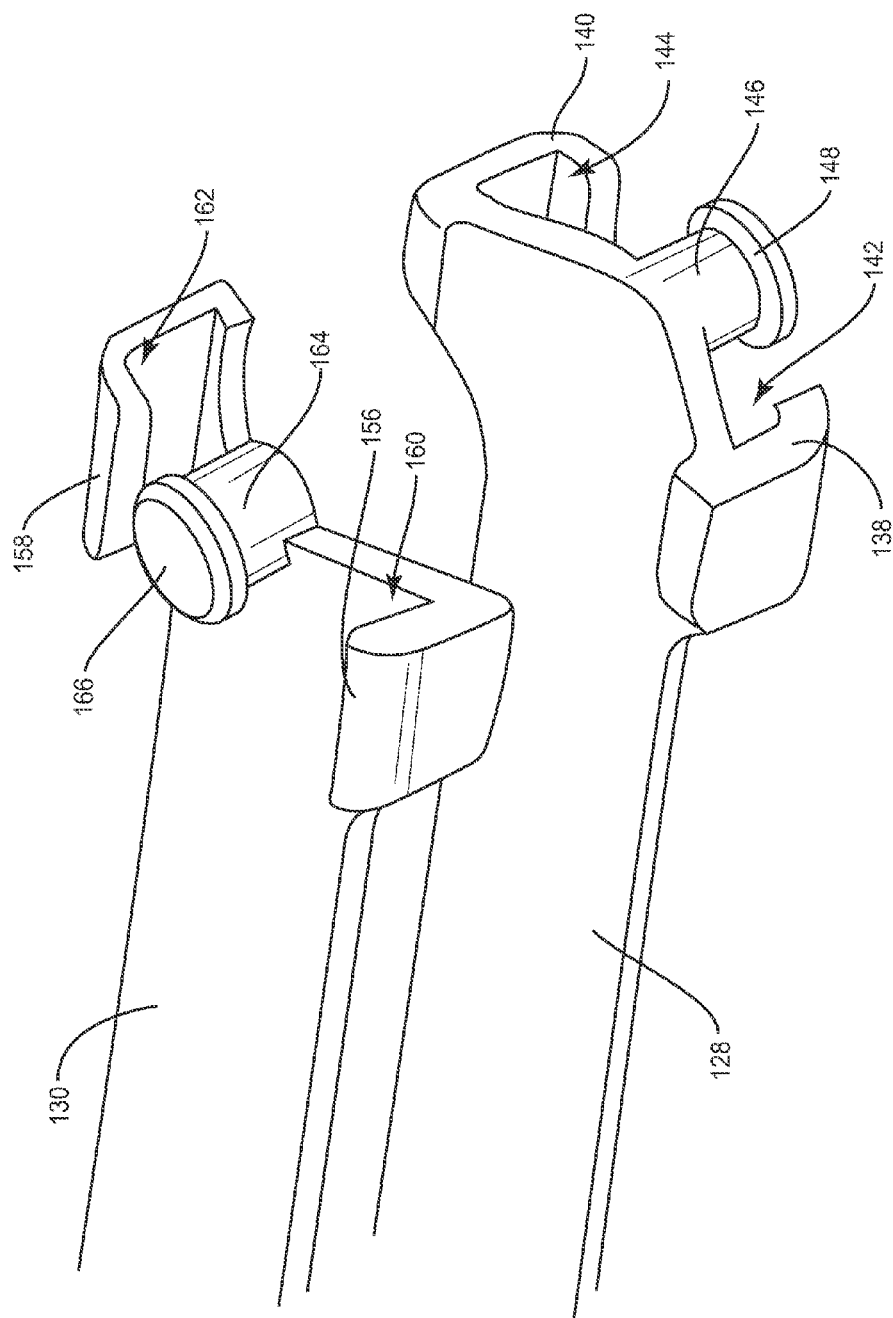
FIG. 8 is a break away perspective view of the component shown in FIG. 7.
Figure 10:
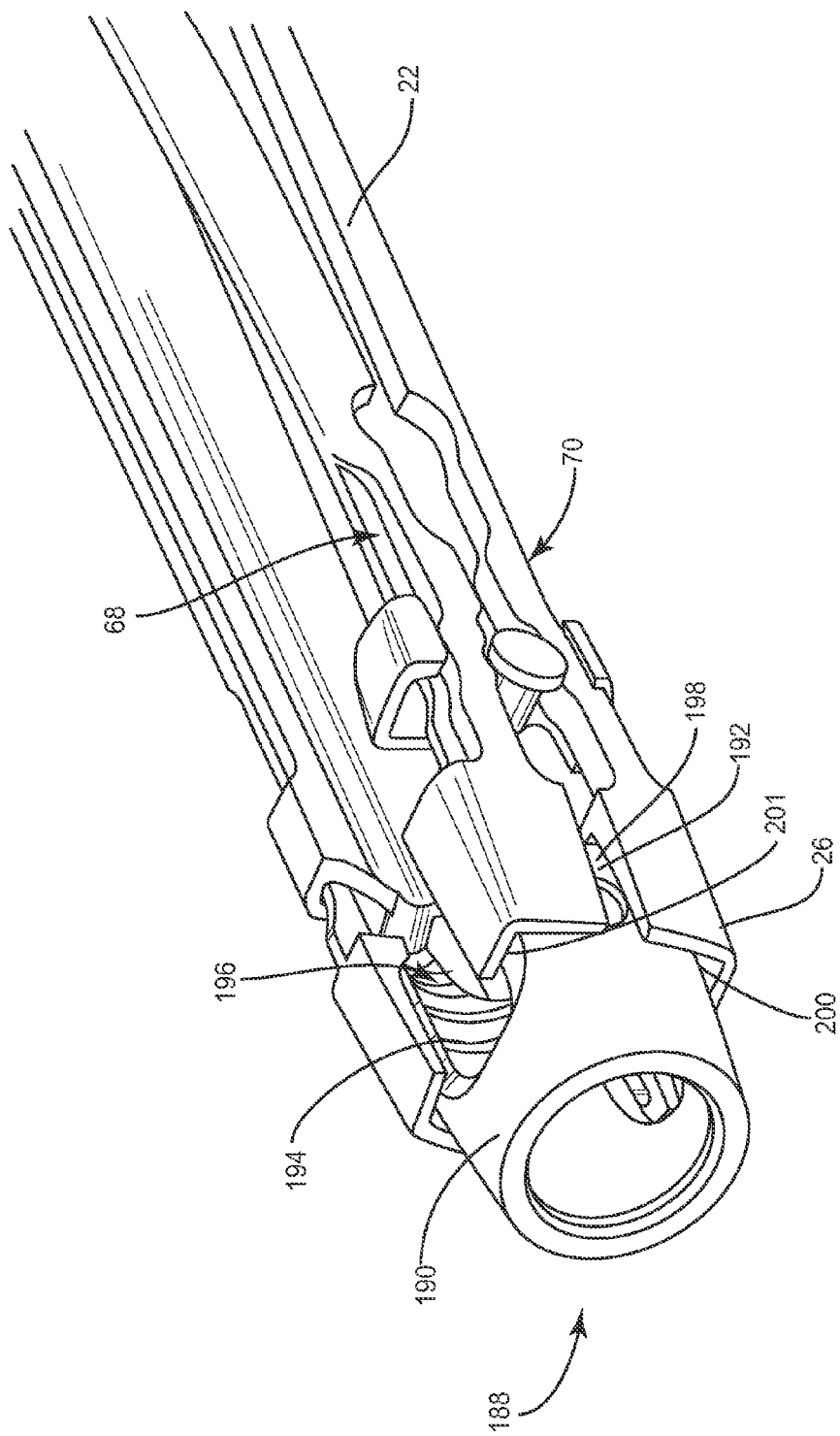
FIG. 10 is a break away perspective view of the system shown in FIG. 1.
Figure 11:
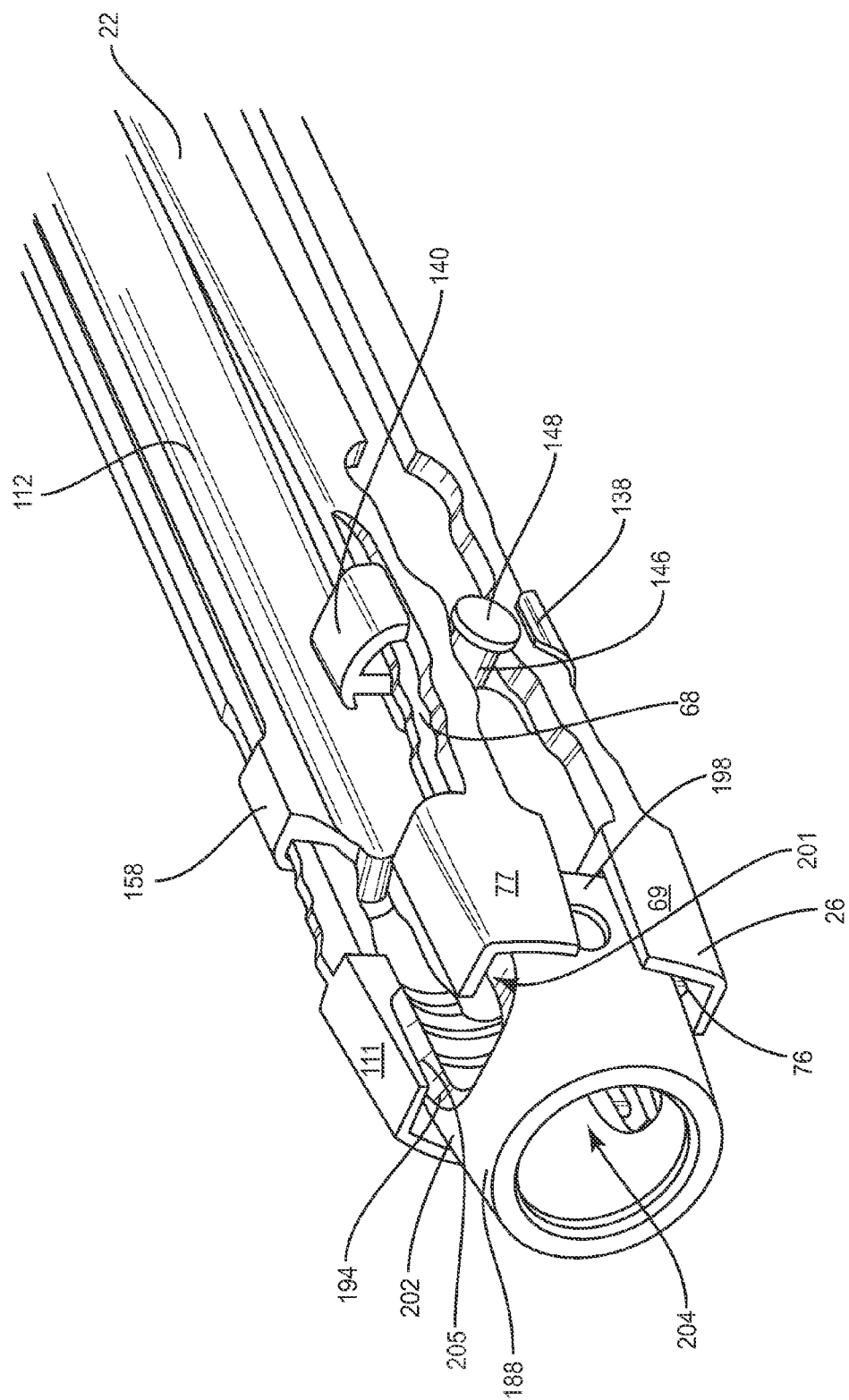
FIG. 11 is a break away perspective view of the system shown in FIG. 1.

Wall 54 defines stepped flange surfaces 68, 70, as shown in FIGS. 6, 10 and 11. Stepped flange surfaces 68, 70 are located on opposing sides of wall 54 near distal end 50. Stepped flange surfaces 68, 70 are configured for engagement with the distal end of an inner sleeve for slidable engagement, as described herein.

Cantilever 72 includes a capture member 69 disposed adjacent a distal end thereof, as shown in FIG. 6. Capture member 69 includes an inner surface 71 that defines an implant cavity configured for disposal of at least a portion of an implant, such as, for example, a bone fastener. Inner surface 71 includes at least one fixation surface, such as, for example, a projection 76 that extends into the implant cavity of capture member 69 to engage the bone fastener for retaining the bone fastener with outer sleeve 22. Inner surface 71 includes a planar face 73 and an arcuate face 75. It is contemplated that all or only a portion of inner surface 71 may have alternate surface configurations to enhance fixation with the bone fastener, such as, for example, dimpled and/or textured. It is contemplated that the projection may include a nail configuration, raised elements and/or spikes to facilitate engagement of the capture member with the bone fastener.

Cantilever 74 includes a capture member 77 disposed adjacent a distal end thereof. Capture member 77 includes an inner surface 79 that defines an implant cavity configured for disposal of at least a portion of an implant, such as, for example, a bone fastener. Inner surface 79 includes at least one fixation surface, such as, for example, a projection 78 that extends into the implant cavity of capture member 77 to engage the bone fastener for retaining the bone fastener with outer sleeve 22. Inner surface 79 includes a planar face 81 and an arcuate face 85. It is contemplated that all or only a portion of inner surface 79 may have alternate surface configurations, similar to those described herein.

Capture member 69 extends from cantilever 72 and capture member 77 extends from cantilever 74 such that members 69, 77 are biased for engagement due to the bias of cantilevers 72, 74. Members 69, 77 are movable between a non-expanded orientation, as shown in FIG. 12, a first expanded orientation, as shown in FIG. 13 and a second expanded orientation, as shown in FIG. 14. In the non-expanded orientation, the surfaces of members 69, 77 are disposed in a flush contacting engagement such that, for example, members 69, 77 capture and/or retain the bone fastener in a locked configuration. Projections 76, 78 engage the bone fastener to releasably lock the bone fastener with members 69, 77.

Members 69, 77 are expandable and separable, via engagement with the inner sleeve as described herein, to dispose members 69, 77 in the expanded orientations. In the first expanded orientation, members 69, 77 are spaced apart such that, for example, members 69, 77 capture and/or retain the bone fastener in a provisional capture configuration. Projections 76, 78 engage the bone fastener to releasably retain the bone fastener with members 69, 77. In the second expanded orientation, members 69, 77 are spaced apart such that, for example, members 69, 77 release and/or eject the bone fastener from members 69, 77. Projections 76, 78 disengage from the bone fastener.

Extension 46 extends between a proximal end 80 and a distal end 82. Intermediate portion 84 is disposed between ends 80, 82. Extension 46 includes a wall 86. It is envisioned that wall 86 may have uniformly increasing or decreasing taper, arcuate, staggered and/or offset portions. Wall 86 includes a first cantilever 104 and a second cantilever 106 extending from proximal end 80. Cantilevers 104, 106 are resiliently biased inwardly towards each other and/or in a convergent configuration to a non-expanded orientation of outer sleeve 22.

Wall 86 includes a first surface 88 and a second surface 90. Surfaces 88, 90 are spaced apart to define an axial cavity 92, similar to axial cavity 60, which is disposed adjacent distal end 82. Axial cavity 92 includes a first portion, such as, for example, a distal portion 94, a second portion, such as, for example, an intermediate portion 96 and a third portion, such as, for example, a proximal portion 98. Axial cavity 92 is configured for slidable disposal of a pin and an inner sleeve, as described herein.

Surfaces 88, 90 are spaced apart distance d1 (FIG. 12) adjacent distal portion 94 in the non-expanded orientation of outer sleeve 22. Outer sleeve 22 is expandable to the first expanded orientation such that surfaces 88, 90 are spaced apart distance d2 (FIG. 13) adjacent distal portion 94. Outer sleeve 22 is expandable to the second expanded orientation such that surfaces 88, 90 are spaced apart a distance d3 (FIG. 14) adjacent distal portion 94. As such, axial cavity 92 can be expanded and contracted adjacent distal portion 94 within a range of expansion between distance d1, distance d2 and distance d3.

Ramps 95 are disposed between distal portion 94 and intermediate portion 96. Ramps 95 extend between a proximal end and a distal end, which define an inclination for engagement with the inner sleeve that facilitates expansion of outer sleeve 22 between the non-expanded orientation, the first expanded orientation and the second expanded orientation.

Surfaces 88, 90 are spaced apart distance d4 (FIG. 12) adjacent intermediate portion 96 in the non-expanded orientation of outer sleeve 22. Outer sleeve 22 is expandable to the first expanded orientation such that surfaces 88, 90 are spaced apart distance d5 (FIG. 13) adjacent intermediate portion 96. Outer sleeve 22 is expandable to the second expanded orientation such that surfaces 88, 90 are spaced apart distance d6 (FIG. 14) adjacent intermediate portion 96. As such, axial cavity 92 can be expanded and contracted adjacent intermediate portion 96 within a range of expansion between distance d4, distance d5 and distance d6.

Ramps 97 are disposed between intermediate portion 96 and proximal portion 98. Ramps 97 extend between a proximal end and a distal end, which define an inclination for engagement with the inner sleeve that facilitates expansion of outer sleeve 22 between the non-expanded orientation, the first expanded orientation and the second expanded orientation.

Surfaces 88, 90 are spaced apart distance d7 (FIG. 12) adjacent proximal portion 98 in the non-expanded orientation of outer sleeve 22. Outer sleeve 22 is expandable to the first expanded orientation, such that surfaces 88, 90 are spaced apart distance d8 (FIG. 13) adjacent proximal portion 98. Outer sleeve 22 is expandable to the second expanded orientation such that surfaces 88, 90 are spaced apart distance d9 (FIG. 14) adjacent proximal portion 98. As such, axial cavity 92 can be expanded and contracted adjacent proximal portion 98 within a range of expansion between distance d7, distance d8 and distance d9.

Wall 86 defines stepped flange surfaces 100. Stepped flange surfaces 100 are located on opposing sides of wall 86 near distal end 82. Stepped flange surfaces 100 are configured for engagement with the distal end of an inner sleeve for slidable engagement, as described herein.

Cantilever 104 includes a capture member 103 disposed adjacent a distal end thereof. Capture member 103 includes an inner surface 105 that defines an implant cavity configured for disposal of at least a portion of an implant, such as, for example, a bone fastener. Inner surface 105 includes at least one fixation surface, such as, for example, a projection 108 that extends into the implant cavity of capture member 103 to engage the bone fastener for retaining the bone fastener with outer sleeve 22. Inner surface 105 includes a planar face 107 and an arcuate face 109. It is contemplated that all or only a portion of inner surface 105 may have alternate surface configurations to enhance fixation with the bone fastener, similar to those described herein.

Cantilever 106 includes a capture member 111 disposed adjacent a distal end thereof. Capture member 111 includes an inner surface 113 that defines an implant cavity configured for disposal of at least a portion of an implant, such as, for example, a bone fastener. Inner surface 113 includes at least one fixation surface, such as, for example, a projection 110 that extends into the implant cavity of capture member 111 to engage the bone fastener for retaining the bone fastener with outer sleeve 22. Inner surface 113 includes a planar face 115 and an arcuate face 117. It is contemplated that all or only a portion of inner surface 113 may have alternate surface configurations, similar to those described herein.

Capture member 103 extends from cantilever 104 and capture member 111 extends from cantilever 106 such that members 103, 111 are biased for engagement due to the bias of cantilevers 104, 106. Members 103, 111 are movable between a non-expanded orientation, a first expanded orientation and a second expanded orientation, similar to members 69, 77 described above. In the non-expanded orientation, the surfaces of members 103, 111 are disposed in a flush contacting engagement to capture and/or retain the bone fastener in a locked configuration. Projections 108, 110 engage the bone fastener to releasably lock the bone fastener with members 103, 111.

Members 103, 111 are expandable and separable, via engagement with the inner sleeve as described herein, to dispose members 103, 111 in the expanded orientations. In the first expanded orientation, members 103, 111 are spaced apart to capture and/or retain the bone fastener in a provisional capture configuration. Projections 108, 110 engage the bone fastener to releasably retain the bone fastener with members 103, 111. In the second expanded orientation, members 103, 111 are spaced apart to release and/or eject the bone fastener from members 103, 111. Projections 108, 110 disengage from the bone fastener.

A second member, such as, for example, an inner sleeve 112 is configured for slidable engagement with outer sleeve 22. Inner sleeve 112 extends along longitudinal axis a and is mounted with outer sleeve 22 for axial translation relative to outer sleeve 12. Inner sleeve 112 has a cylindrical cross-section configuration. It is contemplated that the cross-section of inner sleeve 112 may have various configurations, similar to those alternatives described herein. It is further envisioned that one or all of the surfaces of Inner sleeve 112 may have alternate surface configurations, similar to those alternatives described herein.

Inner sleeve 112 extends between a proximal end 114 and a distal end 116. Proximal end 116 includes body 118. Body 118 defines a biasing member, such as, for example, tab 120. Tab 120 is configured for slidable disposal in opening 30 and is configured for engagement with an actuator, as described herein, to selectively dispose tab 120 in the lock slots of outer sleeve 22. Tab 120 is rotatable and/or pivotable about a pivot point that connects tab 120 with body 118, relative to body 118. Body 118 defines openings 122 and 124. Openings 122, 124 are disposed on parallel sides of body 118. Openings 122, 124 are configured for engagement with an actuator, as described herein.

Inner sleeve 112 includes an implant cavity, such as, for example, channel 126 that extends through Inner sleeve 112. Channel 126 has a cylindrical cross-section configuration. It is contemplated that the cross-section of channel 126 may have various configurations, similar to those alternatives described herein. Channel 126 is configured for disposal of implants, such as spinal rods and screws and/or instruments, such as drivers and reduction devices.

Inner sleeve 112 includes two spaced apart arms, first arm 128 and second arm 130. Arm 128 extends between a proximal end 132 and a distal end 134. Intermediate portion 136 is disposed between ends 132, 134. Arm 128 includes flanges, such as, for example, rails 138, 140. Rails 138, 140 are disposed at distal end 134. Rails 138, 140 define cavities 142, 144. Rails 138, 140 and cavities 142, 144 are located on opposing sides of arm 128. Cavities 142, 144 are configured for disposal of flange surfaces 68, 70 of outer sleeve 22 such that rails 138, 140 slidably engage flange surfaces 68, 70 during, for example, axial translation.

Arm 128 includes a projection, such as, for example, a pin 146. Pin 146 extends outwardly from arm 128. Pin 146 includes a circular flange 148. Pin 146 is configured for engagement with surfaces 56, 58 to expand and contract cantilevers 72, 74 between the non-expanded and expanded orientations. Flange 148 is configured for engagement with an outer surface of cantilevers 72, 74 to retain inner sleeve 112 with outer sleeve 22 during relative axial translation of the components parts.

Arm 130 extends between a proximal end 150 and a distal end 152. Intermediate portion 154 is disposed between ends 150, 152. Arm 130 includes flanges, such as, for example, rails 156, 158. Rails 156, 158 are disposed at distal end 152. Rails 156, 158 define cavities 160, 162. Rails 156, 158 and cavities 160, 162 are located on opposing sides of arm 130. Cavities 160, 162 are configured for disposal of flange surfaces 100, 102 of outer sleeve 22 such that flanges 156, 158 slidably engage flange surfaces 100, 102 during, for example, axial translation.

Arm 130 includes a projection, such as, for example, pin 164. Pin 164 extends outwardly from arm 130. Pin 164 includes a circular flange 166. Pin 164 is configured for engagement with surfaces 88, 90 to expand and contract cantilevers 104, 106 between the non-expanded and expanded orientations. Flange 166 is configured for engagement with an outer surface of cantilevers 104, 106 to retain inner sleeve 112 with outer sleeve 22 during relative axial translation of the components parts. It is envisioned that pins 146, 164 may be transversely oriented relative to the longitudinal axis, such as, for example, perpendicular, angled, and/or may be disposed in parallel orientation relative to the longitudinal axis. It is envisioned that pins 146, 164 can be variously configured with regard to size and shape, and the shape may be rectangular, triangular, polygonal, and hexagonal, for example. It is further envisioned that the projections may comprise a hook, clip and/or key/keyway for slidable engagement with outer sleeve 22.

An actuator 168 is configured for slidable engagement with outer sleeve 22 and for engagement with inner sleeve 112 to cause axial translation of inner sleeve 112 relative to outer sleeve 22, as described herein. Actuator 168 has a tubular cross-section configuration. It is contemplated that the cross-section of actuator 168 may have various configurations, similar to those alternatives described herein.

Actuator 168 extends between a proximal portion 170 and a distal portion 172. An intermediate portion 174 extends between portions 170, 172. Intermediate portion 174 includes openings 176 and 178. Openings 176, 178 are disposed on parallel sides of intermediate portion 174. Openings 176, 178 are configured for disposal of pins 180, 182, which extend through openings 122, 124 of inner sleeve 112. Pins 180, 182 retain actuator 168 with inner sleeve 112 through passages 38, 40. As inner sleeve 112 is manipulated for relative axial translation of the component parts of system 20 between the non-expanded and expanded orientations, pins 180, 182 slide along passages 38, 40.

Actuator 168 includes opening 184. Opening 184 is configured for movable disposal of a button 186. Button 186 is depressible and is biased for movement relative to actuator 168. Button 186 is configured for engagement with tab 120 to pivot tab 120 relative to inner sleeve 112, as described herein. Button 186 is engageable for inward movement to selectively pivot tab 120 out of the lock slots of outer sleeve 22. Button 186 is resiliently biased such that button 186 pivots outwardly to release tab 120 and allow tab 120 to enter and dispose in a selected lock slot.

Spinal implant system 20 includes a bone fastener 188, as shown in FIGS. 10 and 11. Bone fastener 188 includes a proximal portion, such as for example, a receiver 190 and a distal portion, such as, for example, a shaft (not shown). Receiver 190 includes a pair of spaced apart walls 192, 194 defining an implant cavity 196. It is envisioned that walls 192, 194 may have uniformly increasing or decreasing taper, arcuate, staggered and/or offset portions. In one embodiment, the inner surfaces of walls 192, 194 may include internal threads. Internal threads may be configured to receive a set screw (not shown) to fix the position of a vertebral rod, for example, within implant cavity 196 of bone fastener 188. It is envisioned that internal threads may be reverse angle threads such that threads may include a forward face that points down and in toward implant cavity. In one embodiment, implant cavity 196 is generally U-shaped and is configured to receive a cylindrical spinal construct, such as, for example, a vertebral rod. It is contemplated that the cross-section of the vertebral rod may have various configurations, for example, round, oval, rectangular, polygonal, irregular, tapered, offset, staggered, uniform and non-uniform. It is envisioned that implant cavity 196 may have other configurations, including, for example, V-shaped, polygonal, or tapered depending upon the geometry of the spinal construct to be received within implant cavity 196.

Walls 192, 194 include an outer surface 198 defining locking cavities, such as, for example, elongated locking slots 200, 201 and an outer surface 202 defining locking cavities, such as, for example elongated locking slots 204, 205. Locking slots 200, 201 are configured to receive projections 76, 78 and locking slots 204, 205 are configured to receive projections 108, 110, for releasably locking bone fastener 188 with outer sleeve 22. It is envisioned that locking slots 200, 201 and 204, 205 may have other cross-sectional configurations, including, for example, flat bottomed channel, a cut similar to a rack and pinion, V-shaped, W-shaped, polygonal or tapered.

It is further envisioned that one or a plurality of slots 200, 201, 204, 205 may be transversely oriented relative to a longitudinal axis of bone fastener 188, such as, for example, perpendicular, angled, and/or may be disposed in parallel orientation. It is contemplated that slots 200, 201 and 204, 205 allow bone fastener 188 to be captured and retained under tension and lateral compression by outer sleeve 22. It is envisioned that walls 192, 194 may have alternate surface configurations, such as those alternatives described herein.

It is contemplated that the shaft or portions thereof can have various dimensions, for example, with regard to length, width, diameter, and thickness. The shaft is threaded along the length thereof and configured for penetrating tissue. The shaft has a cylindrical cross section configuration and includes an outer surface having an external thread form. It is contemplated that the thread form may include a single thread turn or a plurality of discrete threads. It is further contemplated that other engaging structures may be located on the shaft, such as, for example, a nail configuration, barbs, expanding elements, raised elements and/or spikes to facilitate engagement of the shaft with tissue, such as, for example, vertebrae.

It is envisioned that all or only a portion of the shaft may have alternate cross section configurations, such as, for example, oval, oblong, triangular, square, polygonal, irregular, uniform, non-uniform, offset, staggered, undulating, arcuate, variable and/or tapered. It is contemplated that the outer surface of the shaft may include one or a plurality of openings. It is further contemplated that all or only a portion of the outer surface of the shaft may have alternate surface configurations to enhance fixation with tissue such as, for example, rough, arcuate, undulating, mesh, porous, semi-porous, dimpled and/or textured according to the requirements of a particular application. It is envisioned that all or only a portion of the shaft may be disposed at various orientations, relative to the longitudinal axis of bone fastener 188, such as, for example, transverse, perpendicular and/or other angular orientations such as acute or obtuse and/or may be offset or staggered. It is further envisioned that all or only a portion of the shaft may be cannulated.

In operation, the surfaces of members 69, 77 of extension 44 and members 103, 111 of extension 46 are disposed in a flush contacting engagement in the non-expanded orientation and bone fastener 188 is disposed adjacent distal end 26, as shown in FIG. 12. Pin 146 is disposed with distal portion 62 of axial cavity 60 and pin 152 is similarly disposed with distal portion 94 of axial cavity 92. Tab 120 is aligned with distal lock slot 36 and disposed therein. The outward resilient bias of tab 120 causes tab 120 to be releasably disposed in distal lock slot 36, as shown in FIG. 1, such that inner sleeve 112 and outer sleeve 22 are fixed in the non-expanded orientation.

To attach bone fastener 188 with outer sleeve 22, button 186 is depressed such that button 186 engages tab 120 to overcome the outward bias and pivot tab 120 inwardly from distal lock slot 36. Tab 120 is released from distal lock slot 36 and inner sleeve 112 is freely slidable in axial translation relative to outer sleeve 22. Actuator 168 is manipulated to advance inner sleeve 112 in a proximal direction relative to outer sleeve 22.

Figure 9:
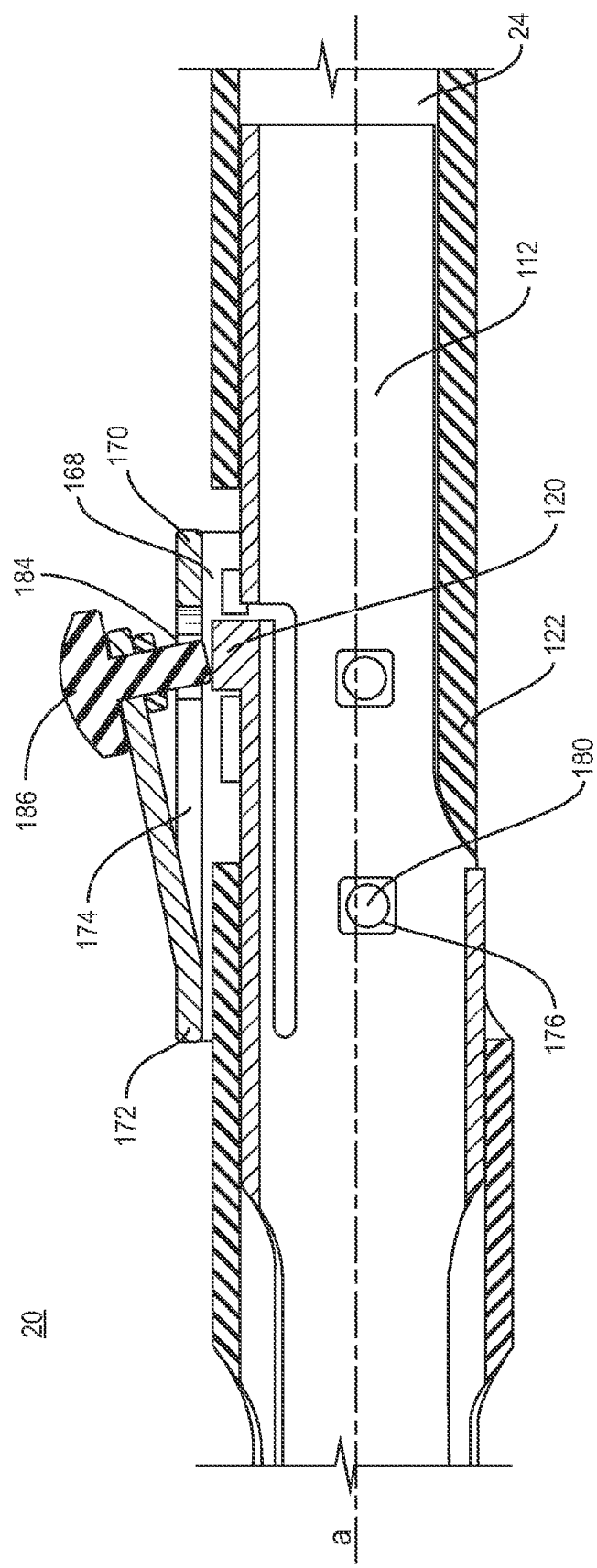
FIG. 9 is a break away cross-section view of the system shown in FIG. 1.

Pins 146, 164 axially translate in a proximal direction within distal portions 62, 94 to engage ramps 61, 95 and drive and space apart the cantilevers of extensions 44, 46. Actuator 168 advances inner sleeve 112 in the proximal direction relative to outer sleeve 22 such that pin 146 is disposed with intermediate portion 64 and pin 152 is similarly disposed with intermediate portion 96. Tab 120 is aligned with intermediate lock slot 34 and disposed therein. The outward resilient bias of tab 120 causes tab 120 to be releasably disposed in intermediate lock slot 34, as shown in FIG. 9, such that inner sleeve 112 and outer sleeve 22 are fixed in the first expanded orientation. In the first expanded orientation, extensions 44, 46 are spaced apart distance d5 adjacent intermediate portions 64, 96. Members 69, 77 and 103, 111 expand and separate, as shown in FIGS. 10 and 13.

Button 186 is depressed such that button 186 engages tab 120 to overcome the outward bias and pivot tab 120 inwardly from intermediate lock slot 34. Tab 120 is released from intermediate lock slot 34 and actuator 168 causes pins 146, 164 to axially translate in the proximal direction within intermediate portions 64, 96 to engage ramps 63, 97 and drive and space apart the cantilevers of extensions 44, 46. Actuator 168 advances inner sleeve 112 in the proximal direction relative to outer sleeve 22 such that pin 146 is disposed with proximal portion 66 and pin 152 is similarly disposed with proximal portion 98. Tab 120 is aligned with proximal lock slot 32 and disposed therein. The outward resilient bias of tab 120 causes tab 120 to be releasably disposed in proximal lock slot 32 such that inner sleeve 112 and outer sleeve 22 are fixed in the second expanded orientation. In the second expanded orientation, extensions 44, 46 are spaced apart distance d9 adjacent proximal portions 66, 98. Members 69, 77 and 103, 111 expand and separate, as shown in FIGS. 11 and 14.

In the second expanded orientation, distal end 26 extends from distal end 116 to engage bone fastener 188. Projections 76, 78 and 108, 110 are manipulated to engage slots 200, 201 and 204, 205, to capture bone fastener 188, as shown in FIG. 14. To provisionally capture bone fastener 188, as shown in FIG. 13, button 186 is depressed such that button 186 engages tab 120 to overcome the outward bias and pivot tab 120 inwardly from proximal lock slot 32. Tab 120 is released from proximal lock slot 32 and actuator 168 causes pins 146, 164 to axially translate in a distal direction. Pins 146, 164 translate distally from proximal portions 66, 98 along ramps 63, 97 into intermediate portions 64, 96 such that the cantilevers of extensions 44, 46 contract. Extensions 44, 46 contract and members 69, 77 and 103, 111 contract to provisionally capture bone fastener 188 in the first expanded orientation. Tab 120 is aligned with intermediate lock slot 34 and disposed therein.

To dispose bone fastener 188 in the locking configuration with outer sleeve 22, as shown in FIG. 12, button 186 is depressed such that button 186 engages tab 120 to overcome the outward bias and pivot tab 120 inwardly from intermediate lock slot 34. Tab 120 is released from intermediate lock slot 34 and actuator 168 causes pins 146, 164 to axially translate in a distal direction. Pins 146, 164 translate distally from intermediate portions 64, 96 along ramps 61, 95 into distal portions 62, 94 such that the cantilevers of extensions 44, 46 contract. Extensions 44, 46 contract and members 69, 77 and 103, 111 contract to dispose bone fastener 188 in the locking configuration with outer sleeve 22 in the non-expanded orientation. Tab 120 is aligned with distal lock slot 36 and disposed therein.

To eject and/or release bone fastener 188 from outer sleeve 22, button 186 is depressed to release tab 120 from distal lock slot 36. Actuator 168 is manipulated to advance inner sleeve 112 in the proximal direction relative to outer sleeve 22. Pins 146, 164 axially translate in the proximal direction within distal portions 62, 94 to engage ramps 61, 95 and space apart the cantilevers of extensions 44, 46 for disposal in intermediate portions 64, 96. Pins 146, 164 axially translate in the proximal direction within intermediate portions 64, 96 to engage ramps 63, 97 and space apart the cantilevers of extensions 44, 46 for disposal within proximal portions 66, 98. Tab 120 is aligned with proximal lock slot 32 and disposed therein such that inner sleeve 112 and outer sleeve 22 are fixed in the second expanded orientation. In the second expanded orientation, members 69, 77 and 103, 111 expand and separate to the second expanded orientation, as shown in FIGS. 11 and 13. Projections 76, 78 and 108, 110 are manipulated to disengage from slots 200, 201 and 204, 205, to eject bone fastener 188 from outer sleeve 22.

Figure 15:
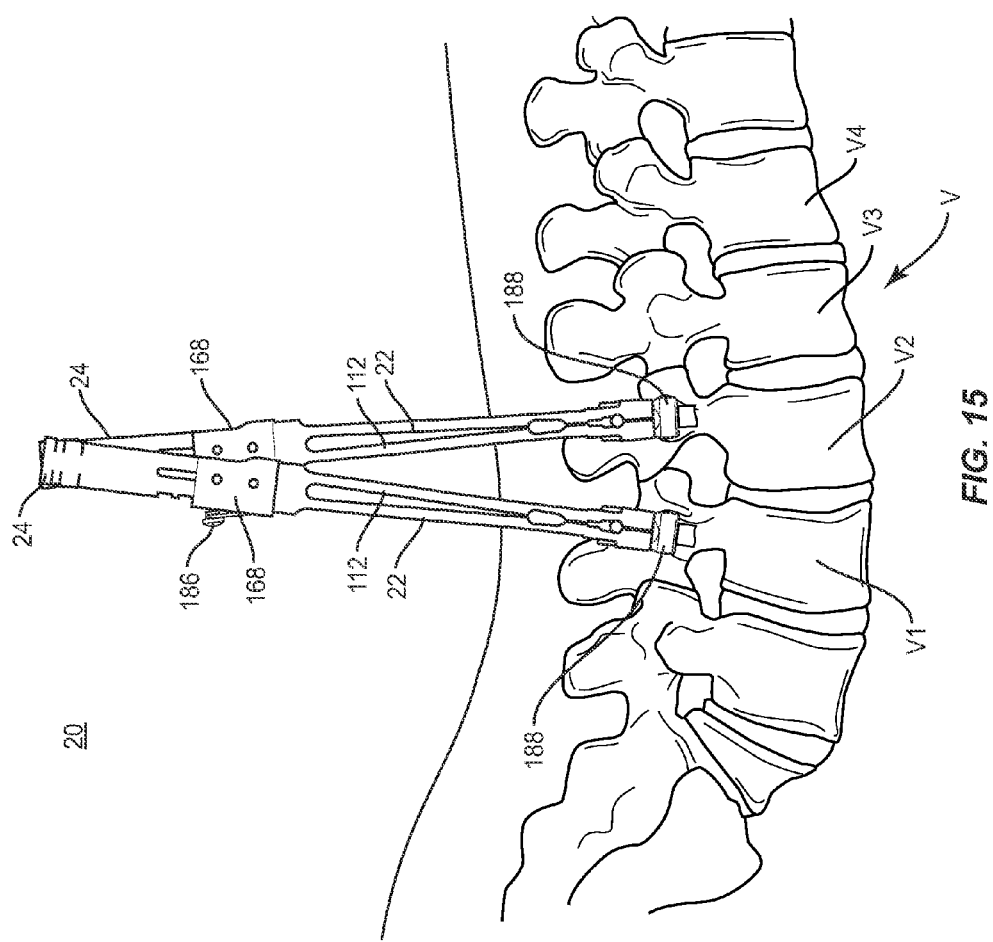
FIG. 15 is a side view of one embodiment of a system in accordance with the principles of the present disclosure disposed with vertebrae.

In assembly, operation and use, spinal implant system 20 is employed with a surgical procedure for treatment of a spinal disorder affecting a section of a spine of a patient, as discussed herein. Spinal implant system 20 may also be employed with other surgical procedures. For example, spinal implant system 20 can be used with a surgical procedure for treatment of a condition or injury of an affected section of the spine including vertebrae V, as shown in FIG. 15.

In use, to treat the affected section of vertebrae V, a medical practitioner obtains access to a surgical site including vertebrae V1, V2 in any appropriate manner, such as through incision and retraction of tissues. It is envisioned that spinal implant system 20 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. Spinal implant system 20 is then employed to augment the surgical treatment. Spinal implant system 20 can be delivered or implanted as a pre-assembled device or can be assembled in situ. Spinal implant system 20 may be completely or partially revised, removed or replaced, for example, removing bone fastener 188, inner sleeve 112 and/or outer sleeve 22, a vertebral rod and/or one or all of the components of spinal implant system 20 during or after the surgical procedure.

Pilot holes or the like are made in vertebrae V1, V2 for receiving the shaft of bone fastener 188. Spinal implant system 20 is disposed adjacent vertebrae V at a surgical site and the components of spinal implant system 20 are manipulable to drive, torque, insert or otherwise connect bone fastener 188 to vertebrae and/or dispose a vertebral construct, such as, for example, a vertebral rod (not shown) with bone fastener 188, according to the particular requirements of the surgical treatment.

Extensions 44, 46 are disposed in the non-expanded orientation, as described above, and bone fastener 188 is disposed adjacent distal end 26. To attach bone fastener 188 with outer sleeve 22, button 186 releases tab 120 from distal lock slot 36 and actuator 168 advances inner sleeve 112 in a proximal direction relative to outer sleeve 22. Pins 146, 164 drive and space apart the cantilevers of extensions 44, 46 for disposal within proximal portions 66, 98. Tab 120 is aligned with proximal lock slot 32 and disposed therein such that inner sleeve 112 and outer sleeve 22 are fixed in the second expanded orientation, as described above. In the second expanded orientation, extensions 44, 46 are spaced apart, and members 69, 77 and 103, 111 expand and separate, as shown in FIGS. 11 and 14.

In the second expanded orientation, distal end 26 extends from distal end 116 to engage bone fastener 188. Projections 76, 78 and 108, 110 are manipulated to engage slots 200, 201 and 204, 205, to capture bone fastener 188, as shown in FIG. 14. To provisionally capture bone fastener 188, as shown in FIG. 13, button 186 releases tab 120 from distal lock slot 36 and actuator 168 advances inner sleeve 112 in a distal direction relative to outer sleeve 22. Pins 146, 164 translate distally such that the cantilevers of extensions 44, 46 contract. Extensions 44, 46 contract and members 69, 77 and 103, 111 contract to provisionally capture bone fastener 188 in the first expanded orientation. Tab 120 is aligned with intermediate lock slot 34 and disposed therein. In one embodiment, the components of system 20 are disposed in a locking configuration, as described above and shown in FIG. 12, such that inner sleeve 112, fixed with bone fastener 188, may apply torque and/or rotation to bone fastener 188 for driving the shaft into vertebrae V.

To eject and/or release bone fastener 188 from outer sleeve 22, button 186 releases tab 120 from distal lock slot 36 or intermediate lock slot 34 and actuator 168 advances inner sleeve 112 in a proximal direction relative to outer sleeve 22. Pins 146, 164 drive and space apart the cantilevers of extensions 44, 46 for disposal within proximal portions 66, 98. Tab 120 is aligned with proximal lock slot 32 and disposed therein such that inner sleeve 112 and outer sleeve 22 are fixed in the second expanded orientation, as described above. In the second expanded orientation, extensions 44, 46 are spaced apart, and members 69, 77 and 103, 111 expand and separate, as shown in FIGS. 11 and 14, such that projections 76, 78 and 108, 110 are manipulated to disengage from slots 200, 201 and 204, 205, and to eject bone fastener 188 from outer sleeve 22. Upon completion of the procedure, the surgical instruments and assemblies are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An extender comprising:
   an outer member defining a longitudinal axis and including a body defining a lateral opening, the outer member further including a first extension defining a first axial cavity and a second extension defining a second axial cavity, each of the axial cavities including a first portion, a second portion and a third portion; and
   an inner member including a body defining a tab configured for disposal in the lateral opening, the inner member further including a first arm having a first projection disposed for movement within the first axial cavity and a second arm having a second projection disposed for movement within the second axial cavity,
   wherein the inner member is configured for axial translation relative to the outer member such that the projections are disposable between a first position such that the projections are disposed with the first portions of the respective axial cavity and the outer member is disposed in a non-expanded orientation, a second position such that projections are disposed with the second portions of the respective axial cavity and the outer member is disposed in an expanded orientation, and a third position such that the projections are disposed with the third portions of the respective axial cavity and the outer member is disposed in an expanded orientation,
   wherein the lateral opening includes a locking cavity comprising a plurality of lock slots such that the tab is movable into the locking cavity to fix the inner member relative to the outer member in each of the positions.

2. An extender as recited in claim 1, wherein the tab is rotatable relative to the inner member body into the locking cavity.

3. An extender as recited in claim 1, wherein the plurality of lock slots include a first lock slot, a second lock slot and a third lock slot, and the tab is resilient such that the tab is rotatable relative to the inner member body into the first lock slot to fix the inner member relative to the outer member in the first position, the second lock slot being configured to fix the inner member relative to the outer member in the second position and the third lock slot being configured to fix the inner member relative to the outer member in the third position.

4. An extender as recited in claim 1, further comprising an actuator connected to the inner member and defining a movable part engageable with the tab.

5. An extender as recited in claim 1, further comprising an actuator connected to the inner member and defining a part biased for movement relative to the actuator for engagement with the tab to rotate the tab relative to the inner member body from at least one of the positions.

6. An extender as recited in claim 1, further comprising an actuator defining a resilient button, wherein the plurality of lock slots include a first lock slot, a second lock slot and a third lock slot and the tab is resilient such that the button engages the tab to rotate the tab relative to the inner member body into the first lock slot to fix the inner member relative to the outer member in the first position, the second lock slot to fix the inner member relative to the outer member in the second position and the third lock slot to fix the inner member relative to the outer member in the third position.

7. An extender as recited in claim 1, wherein the first extension includes a first wall that defines a stepped flange surface and the first arm includes a first flange that defines a first flange cavity configured for disposal of the first flange such that the first flange slidably engages the stepped flange surface during the axial translation.

8. An extender as recited in claim 1, wherein the first extension includes a first wall having a stepped surface that defines at least one of the first portion and the second portion of the first axial cavity.

9. An extender as recited in claim 1, wherein the first extension includes a first wall having a first stepped surface that defines the first portion of the first axial cavity and a second stepped surface that defines the second portion of the first axial cavity.

10. An extender as recited in claim 1, wherein the first extension extends to a distal end and includes a first cantilever and a second cantilever.

11. An extender as recited in claim 1, wherein the first extension extends to a distal end and includes a first cantilever and a second cantilever, the cantilevers being disposed in a substantially flush engagement in the non-expanded orientation and spaced apart in the expanded orientation.

12. An extender as recited in claim 1, wherein the first projection extends outwardly and includes a circular flange configured to engage the first extension.

13. A method for treating a spine comprising:
providing the extender recited in claim 1, wherein the plurality of lock slots comprise a distal lock slot, a proximal lock slot and an intermediate lock slot between the distal and proximal lock slots, the tab being disposed in the proximal lock slot such that the inner sleeve and the outer sleeve are fixed in the second expanded orientation;
engaging a bone fastener with a distal end of the outer member such that the bone fastener is movable relative to the outer member;
engaging a button to release the tab from the proximal lock slot;
translating the inner sleeve in a distal direction relative to the outer sleeve such that the tab is aligned with the intermediate lock slot and disposed therein such that the inner sleeve and the outer sleeve are fixed in the first expanded orientation and the bone fastener is provisionally fixed relative to the outer member;
engaging the button to release the tab from the intermediate lock slot; and
translating the inner sleeve in a distal direction relative to the outer sleeve such that the tab is aligned with the distal lock slot and disposed therein such that the inner sleeve and the outer sleeve are fixed in the second expanded orientation and the bone fastener is fixed relative to the outer member in a locking configuration.

14. An extender comprising:
an outer member defining a longitudinal axis and including a body comprising a lateral opening, the outer member further including a first extension extending from the body and defining a first axial cavity and a second extension extending from the body and defining a second axial cavity, each of the axial cavities including a first portion having a first dimension, a second portion having a second dimension and a third portion having a third dimension, the first dimension being greater than the second dimension and the second dimension being greater than the third dimension; and
an inner member including a body including a first tab configured for disposal in the lateral opening, the inner member further including a first arm having a first outward projection disposed for movement within the first axial cavity and a second arm having a second outward projection disposed for movement within the second axial cavity,
wherein the inner member is configured for axial translation relative to the outer member such that the projections are disposable between a first position such that the projections are disposed with the first portions of the respective axial cavity and the outer member is disposed in a non-expanded orientation, a second position such that the projections are disposed with the second portions of the respective axial cavity and the outer member is disposed is disposed in a first expanded orientation, and a third position such that the projections are disposed with the third portions of the respective axial cavity and the outer member is disposed in a second expanded orientation,
wherein the lateral opening includes a locking cavity comprising a plurality of lock slots such that the tab is movable into the locking cavity to fix the inner member relative to the outer member in each of the positions.

15. An extender as recited in claim 14, wherein the plurality of lock slots comprise a proximal lock slot, an intermediate lock slot and a distal lock slot, and the tab is rotatable relative to the inner member body into the distal lock slot to fix the inner member relative to the outer member in the first position, the intermediate lock slot to fix the inner member relative to the outer member in the second position and the proximal lock slot to fix the inner member relative to the outer member in the third position.

16. An extender as recited in claim 14, further comprising an actuator defining a resilient button, wherein the plurality of lock slots comprise proximal lock slot, an intermediate lock slot and a distal lock slot and the tab is rotatable relative to the inner member body into the distal lock slot to fix the inner member relative to the outer member in the first position, the intermediate lock slot to fix the inner member relative to the outer member in the second position and the proximal lock slot to fix the inner member relative to the outer member in the third position, the actuator being engageable with the tab to rotate the tab relative to the inner member body from the lock slots.

17. An extender as recited in claim 14, wherein the first extension includes a first wall that defines a stepped flange surface and the first arm includes a first flange that defines a first flange cavity configured for disposal of the first flange such that the first flange slidably engages the stepped flange surface during the axial translation.

18. An extender as recited in claim 14, wherein the first extension includes a first wall having a first stepped surface that defines the first portion of the first axial cavity and a second stepped surface that defines the second portion of the first axial cavity.

19. An extender as recited in claim 14, wherein the first extension extends to a distal end and includes a first cantilever and a second cantilever, the cantilevers being disposed in a substantially flush engagement in the non-expanded orientation and spaced apart in the expanded orientation.

20. A spinal implant system comprising:
an extender comprising an outer sleeve extending between a proximal end and a distal end and defining a longitudinal axis and an inner sleeve extending between a proximal end and a distal end,
the outer sleeve including a body defining a lateral opening, the lateral opening including a proximal lock slot, an intermediate lock slot and a distal lock slot disposed in series along the longitudinal axis, the outer sleeve further including a first wall extending from the body and having a first extension including a first cantilever and a second cantilever defining a first axial cavity therebetween and a second extension including a first cantilever and a second cantilever defining a second axial cavity therebetween, each of the axial cavities including a distal portion having a first dimension, an intermediate portion having a second dimension and a proximal portion having a third dimension, the first dimension being greater than the second dimension and the second dimension being greater than the third dimension, each of the cantilevers including a capture surface,
the inner sleeve including a body defining a resilient tab such that the tab is rotatable relative to the inner member body, the inner sleeve further including a first arm having a first outward projection disposed for movement within the first axial cavity and a second arm having a second outward projection disposed for movement within the second axial cavity, the first arm includes a first flange that defines a first flange cavity configured for disposal of the first extension such that the first flange slidably engages the first extension during axial translation, the second arm includes a second flange that defines a second flange cavity configured for disposal of the second extension such that the second flange slidably engages the second extension during axial translation,
a tubular actuator disposed about the outer sleeve and connected with the inner sleeve, the actuator defining a resilient button rotatable relative to the actuator; and
a bone fastener including a proximal portion that defines an implant cavity and a distal portion configured to penetrate tissue,
wherein the inner sleeve is configured for axial translation relative to the outer sleeve such that the outward projections are disposable between a first position such that the outward projections are disposed with the distal portions of the respective axial cavity and the outer sleeve is disposed in a locking orientation, a second position such that the outward projections are disposed with the intermediate portions of the respective axial cavity and the outer sleeve is disposed in a capture orientation, and a third position such that the outward projections are is disposed with the second portions of the respective axial cavity and the outer sleeve is disposed in an eject orientation,
wherein the button engages the tab to rotate the tab relative to the inner sleeve body into the distal lock slot to fix the inner member relative to the outer member in the first position, the intermediate lock slot to fix the inner member relative to the outer member in the second position and the proximal lock slot to fix the inner member relative to the outer member in the third position.

* * * * *